US009572768B2

(12) United States Patent
Doucet et al.

(10) Patent No.: US 9,572,768 B2
(45) Date of Patent: Feb. 21, 2017

(54) COSMETIC COMPOSITION FOR USE IN INCREASING THE COLLAGEN SYNTHESIS IN SKIN CELLS

(75) Inventors: Olivier Doucet, Roquebrune Cap Martin (FR); Muriel Pujos, Nice (FR); Cécile Robert, Nice (FR); Dorothée Bernini, Monaco (MC)

(73) Assignee: Coty Germany GmbH, Mainz (DE)

( * ) Notice: Subject to any disclaimer, the term of this patent is extended or adjusted under 35 U.S.C. 154(b) by 231 days.

(21) Appl. No.: 14/112,782

(22) PCT Filed: Apr. 18, 2012

(86) PCT No.: PCT/EP2012/057029
§ 371 (c)(1),
(2), (4) Date: Jan. 3, 2014

(87) PCT Pub. No.: WO2012/143364
PCT Pub. Date: Oct. 26, 2012

(65) Prior Publication Data
US 2014/0127286 A1    May 8, 2014

(30) Foreign Application Priority Data
Apr. 20, 2011   (EP) .................................. 11163232

(51) Int. Cl.
| | | |
|---|---|---|
| *A61K 8/02* | (2006.01) | |
| *A61K 8/99* | (2006.01) | |
| *A61K 8/64* | (2006.01) | |
| *A61K 8/97* | (2006.01) | |
| *A61Q 19/00* | (2006.01) | |
| *A61Q 19/08* | (2006.01) | |

(52) U.S. Cl.
CPC .................. *A61K 8/99* (2013.01); *A61K 8/64* (2013.01); *A61K 8/97* (2013.01); *A61K 8/975* (2013.01); *A61Q 19/00* (2013.01); *A61Q 19/08* (2013.01); *A61K 2800/70* (2013.01)

(58) Field of Classification Search
None
See application file for complete search history.

(56) References Cited

U.S. PATENT DOCUMENTS

| 5,853,705 | A | 12/1998 | Nakayama et al. | |
|---|---|---|---|---|
| 2004/0136945 | A1 | 7/2004 | Nizard et al. | |
| 2007/0110731 | A1* | 5/2007 | Riley | A61K 31/728 424/93.7 |
| 2010/0160244 | A1 | 6/2010 | Nimni et al. | |
| 2011/0294876 | A1* | 12/2011 | Kuper | A23G 3/36 514/465 |
| 2012/0040912 | A1 | 2/2012 | Dal Farra et al. | |
| 2012/0093745 | A1 | 4/2012 | Dal Farra et al. | |

FOREIGN PATENT DOCUMENTS

| EP | 2113241 | * | 11/2009 | ............... A61K 8/11 |
|---|---|---|---|---|
| EP | 2113241 A2 | * | 11/2009 | ............... A61K 8/11 |
| JP | 2010006743 | | 1/2010 | |
| WO | 02102347 | | 12/2002 | |
| WO | 2009018126 | | 2/2009 | |
| WO | 2009058613 | | 5/2009 | |
| WO | 2010122244 | | 10/2010 | |
| WO | WO-2012143364 | | 10/2012 | |

OTHER PUBLICATIONS

Anti-aging products that address Nobel-winning telomeres, Ingredients in Dermasilk, retrieved from URL:<https://www.truthinaging.com/review/products-with-teprenone>, Oct. 15, 2009.*
"Concentrato antirughe antiwrinkle cream", GNPD Database (Jan. 2004): 246771. (2 pages).
Dibon, "Inflammation and aging", GCI Magazine (2011). (2 pages).
International Search Report and Written Opinion mailed on Oct. 15, 2013 in PCT Application No. PCT/EP2012/057029. (12 pages).
"Lift Cream", GNPD Database (Jun. 2008): 931617. (2 pages).
"European Application Serial No. 12720819.7, Office Action mailed Oct. 18, 2016", 5 pgs.

* cited by examiner

*Primary Examiner* — Nannette Holloman
(74) *Attorney, Agent, or Firm* — Schwegman Lundberg & Woessner, P.A.

(57) ABSTRACT

The invention refers to a cosmetic composition for increasing collagen synthesis in skin cells comprising 0.001-0.5 wt % of a *Phaeodactylum tricornutum* extract, 0.00001-2.0 wt % of Dimer Tripeptide-43 or Hydrolyzed Rice Protein, and cosmetic auxiliaries. The cosmetic composition comprising the combination of both components has an synergistic effect on collagen I synthesis in skin cells and has a booster effect to other substances which are known to have an enhancing effect to collagen I synthesis.

12 Claims, 6 Drawing Sheets

Significant improvement of Dermis density following 28 days of repeated application

COSMETIC COMPOSITION FOR USE IN INCREASING THE COLLAGEN SYNTHESIS IN SKIN CELLS

This application is a §371 national phase filing of PCT/EP2012/057029, filed Apr. 18, 2012, which claims priority to and the benefit of EP 11 163 232.9, filed Apr. 20, 2011, both of which are herein incorporated by reference in their entirety.

The invention refers to a composition from the field of cosmetics with increasing effect on collagen synthesis in skin.

There are a number of inventive proposals to enhance the collagen synthesis because collagen, as the most abundant protein in mammals, plays an essential structural role and helps to provide tissues with mechanical strength. There are a number of publications that disclose the use of plant extracts for that purpose, e.g. JP 2010006743 which uses pine bark extract plus collagen and a calcium or sodium compound. WO 2009/058613 refers to China Seed Oil and Opuntia Ficus Indica extract for stimulation of collagen synthesis.

Other proposals are directed to the use of peptides or amino acids. US 2010160244 discloses a mixture of essential amino acids, an antioxidant, an organic penetrant and a supplemental source of sulphur. WO 2009/018126 refers to a collagen-related polypeptide with the basic sequence of Gly-Pro-J wherein J is Pro or Hyp and having collagen-mimetic properties.

The aim of the invention is to enhance collagen synthesis in skin and to provide a cosmetic composition for this purpose.

The inventors of the present invention have found that the collagen synthesis in skin can be enhanced using a composition which comprises 0.001-0.5 wt % of a *Phaeodactylum tricornutum* extract;

0.00001-2.0 wt %, preferably 0.00005-2.0 wt % of Dimer Tripeptide-43 or Hydrolyzed Rice Protein;

and one or more cosmetic auxiliaries up to a total of 100 wt % of the composition. The given percentages of the components of the composition generally relate to the total weight of the composition.

A known commercial product of the *Phaeodactylum tricornutum* extract is carpylic/capric triglyceride & *Phaeodactylum tricornutum* extract & tocopherol (INCI name) such as Megassane® (trade name) of Soliance, Paris, France. The use of the *Phaeodactylum tricornutum* algae extract as cosmetic agent is also described in WO 02/080876 A2. The *Phaeodactylum tricornutum* extract increases the activity of proteasomes and helps to protect skin cells against harmful effects of UV exposure by influencing the proteasome activity in cells.

The *Phaeodactylum tricornutum* extract is prepared by digestion of the cultivated marine phytoplankton by NaOH and ethanol and after that extraction with a saturated hydrocarbon such as heptane or hexane and admixture of a strong acid such as sulphuric acid, for instance in a temperature range of 30-100° C. and filtration and evaporation. The *Phaeodactylum tricornutum* extract increases the activity of proteasomes and helps under UV stress to protect cells by influencing the proteasome activity in the cells.

According to the invention preferred ranges of carpylic/capric triglyceride & *Phaeodactylum tricornutum* extract & tocopherol are 0.01-0.5 wt %, especially 0.03-0.2 wt %. The *Phaeodactylum tricornutum* extract is contained in the composition used in the invention from 0.001 to 0.5 wt %.

A known commercial product of dimer tripeptide-43 is Prolixir S20® (trade name, ISP Vincience, France) or aqua & butylene glycol & dimer tripeptide-43 (INCI name). Prolixir S20 contains 0.01% of dimer tripeptide-43. A known commercial product of hydrolyzed rice protein is Prolixir ICE (trade name, ISP Vincience, France) or aqua & glycerin & hydrolyzed rice protein (INCI name). Prolixir ICE comprises 0.5% of hydrolyzed rice protein. Dimer tripeptide-43 and hydrolyzed rice protein are plant hydrolysates as described in WO 2010/122244 A1 and enriched with bioactive peptides of general formula (1)

wherein $X_1$ is an asparagine, a lysine, an aspartate, a valine, an arginine, or is absent;

$X_2$ is a histidine, a lysine, an arginine, or is absent.

Preferably the peptidic hydrolysates are rich in the following bioactive peptides: Arg-Asp-Cys-Arg-Arg; Asn-Asp-Cys-Arg-Lys; Asp-Cys-Arg-His; Val-Asp-Cys-Arg; Asp-Cys-Arg. That means, the enriched peptidic hydrolysates are composed of peptides with a molecular weight of less than 6 kDa and are enriched in bioactive peptides containing 3 to 5 amino acids comprising at least one aspartic acid residue, one cysteine residue and one arginine residue.

The dimer tripeptide-43 hydrolysate and hydrolyzed rice protein hydrolysate are prepared by hydrolysis of corn (*Zea mays* L.) or pea (*Pisum sativum*) and rice (*Oryza sativa* L.) as described in WO 2010/122244 A1 which is herewith incorporated by reference. The hydrolysates are described to be proteasome activators and have effects on non-functional proteins and the ubiquitin-proteasome System.

According to the invention preferred ranges of aqua & butylene glycol & dimer tripeptide-43 and aqua & glycerin & hydrolyzed rice protein are 0.1 to 1.0 wt %.

Surprisingly, a combination of the *Phaeodactylum tricornutum* extract with dimer tripeptide-43 or hydrolyzed rice protein show a significantly enhanced effect on the collagen-I synthesis surpassing the effect of collagen-I synthesis-enhancing substances according to a Western Blot Test on normal human fibroblasts. Clinical studies on dermis density have revealed that the composition of the invention provides a significant improvement of dermis density after 4 weeks of twice daily application.

In a further embodiment of the invention the cosmetic composition for use in increasing the collagen synthesis in skin comprises (1) 0.001-0.5% wt % of a *Phaeodactylum tricornutum* extract;

(2) 0.00001-2.0 wt %, preferably 0.00005-2.0 wt % of dimer tripeptide-43 or hydrolyzed rice protein;

(3) 0.1-9.0 wt % of one or more substances which have an enhancing effect on collagen-I synthesis; all concentrations are related to the total weight of the composition; and (4) further cosmetic auxiliaries or mixtures thereof up to a total of 100 wt % of the composition.

Substances which have an enhancing effect on the collagen-I synthesis are e.g. several peptides such as dipeptides, hexapeptides; extracts of other plants such as *areca* nut (*Areca Catechu* Seed Extract), *Panax Japonicus* Extract, White Tea Extract, Rose Fruit Extract, *Kigelia Africana* Fruit Extract; or a special oil such as Chia Seed Oil or the product hydrolysed soy flour. Preferred substances are a Tyr-Arg dipeptide such as acetyl dipeptide-1 cetyl ester (e.g. Calmosensine®), hexapeptide-11 (e.g. Peptamide 6®), hydrolysed soy flour (e.g. Raffermine®) and *Kigelia Africana* Fruit Extract (Kigeline®) or mixtures thereof.

Hydrolysed soy flour is known to promote the contraction of the collagen fibres and protect the elastin fibres from enzymatic attack.

A preferred Val-Gly-Val-Ala-Pro-Gly hexapeptide is palmitoyl-VGVAPG peptide or hexapeptide-11.

Preferred dipeptides are N-acetyl-Tyr-Arg hexadodecyl ester or acetyl dipeptide-1 cetyl ester.

A further preferred substance with an enhancing effect on the collagen-I synthesis is *Kigelia Africana* Fruit Extract, especially in a mixture with hexapeptide-11, acetyl dipeptide-1 cetyl ester and hydrolysed soy flour.

The enhancing effect of these substances on the collagen-I synthesis is strongly boosted by adding a combination of *Phaeodactylum tricornutum* extract and dimer tripeptide-43 or hydrolyzed rice protein. This is evidenced by comparative tests carried out by the applicant.

Cosmetic auxiliaries which may be contained in the composition are e.g. one or more antioxidants, radical scavengers, inorganic and organic sunscreens (UV filters), emulsifying agents, pigments, preservatives, gel formers, dyes, perfumes, stabilisers, film-forming agents, emollients, conditioning agents, moisturizing substances, chelating agents, SPF boosters, humectants, anti-inflammatory natural active agents, pH regulators etc.

Specially preferred are antioxidants, radical scavengers, UV filters, emulsifying agents, moisturizing substances, gel formers, SPF boosters, emollients, silicone oils, emulsion stabilisers, pH regulators, preservatives.

Additional dermatological or cosmetic auxiliaries which can be used in the composition include e.g. water, vitamins, enzymes, other plant extracts, polymers, enzymes, phospholipids, panthenol, allantoin, synthetic ethers and esters, fatty acids, monovalent and multivalent alcohols, silicones, minerals, further oils especially plant oils, waxes, biotechnological extracts. Biotechnological extracts are e.g. CLR Repair Complex or Yeast Complex B (both of CLR, Chem. Lab. Dr. Kurt Richter GmbH, Berlin, Germany); Stimulhyal, Primalhyal 50 or 300 (all of SOLIANCE, Paris, France).

Specially preferred are water, vitamins, other plant extracts and mixtures of extracts, synthetic polymers, esters, ethers, fatty acids, monovalent and multivalent alcohols, silicones, silicates, waxes.

A cosmetic composition of the invention can—as mentioned—advantageously also contain antioxidants. Antioxidants include e. g. vitamins such as for instance vitamin C and derivatives thereof, for example, ascorbic acetate, phosphate, and palmitate; folic acid and derivatives thereof, vitamin E and derivatives thereof, such as tocopherol acetate; flavones or flavonoids; furthermore amino acids, such as histidine, tyrosine, tryptophan, and derivatives thereof; imidazole such as cis- or trans-uro-caninic acid and their derivatives; peptides such as D,L-carnosine, D-carnosine, L-carnosine and their derivatives; hyaluronic acid; lycopene; uric acid and derivatives thereof; α-hydroxy acids such as citric acid, lactic acid, malic acid; α-hydroxy fatty acids such as palmitic acid, phytic acid, lactoferrin; mannose and their derivatives; liponic acid and their derivatives such as dihydro liponic acid; ferulic acid and their derivatives; thiols such as glutathione, cysteine and cystine.

The addition of hyaluronic acid and vitamin E is especially preferred.

A further preferred radical scavenger in connection with the cosmetic composition is a mixture of the following plant extracts: *Angelica archangelica, Camellia Sinensis* Leaf Extract, *Pongamia Pinnata* Seed Extract, *Coffea Arabica* Seed Extract in an alcoholic preparation, in an encapsulated liposomale version or in a non-encapsulated oily version. All versions may additionally contain Citrus Auranthium (Bitter Orange) Peel Extract. A special radical scavenger mixture of liposomic encapsulated plants comprises 1-4% Green Tea Leaf Extract, 1-4% green coffee, 1-4% *Pongamia Pinnata* Seed Extract, 1-4% *Angelica Archangelica* Root Extract, 2-10% phospholipids in an aqueous-alcoholic suspension wherein the alcohol content is in the range of 4-12%, wherein all concentrations are related to the weight of the radical scavenger mixture.

The share of such a radical scavenger mixture in a cosmetic composition of the invention is 0.01-1.0% by weight, related to the total weight of the composition.

The cosmetic composition of the invention can be used in different cosmetic products such as lotions, oils, creams, day creams, night creams, day care products with UV protection, gels, masks, balms, powders, eye-liftings, tan glows, tinted creams, fillers, tissue masks, pre-sun products, sun products, after-sun products, self-tans, make-ups, compact powders, photoprotecting products, sprays, makeup-removers, cleansers, target products, primers, blush powders, bath products such as shower and bath gels or salts, lipsticks, deo sticks.

Emulsion products include multiple emulsions, micro emulsions and nano emulsions in the form of W/O, O/W, W/Si, Si/W, W/O/W, O/W/O, O/W/Si and W/Si/W emulsions (O=Oil, W=Water, Si=Silicone). Other products such as anhydrous systems like Si/O are also included.

Pre-sun products are e.g. pre-sun gels, pre-sun lotions, pre-sun creams or pre-sun oils. Sun products are gels, creams, lotions, oils, sprays or daily protective skin care products with different Sun Protection Factors (SPF) in the range from SPF 2 to SPF 50, e.g. SPF 6, SPF 10, SPF 15, SPF 20, SPF 25, SPF 30, SPF 50 and SPF 50+. The different SPFs are dependent on the kind and amount of UV filter substances.

Suitable cosmetic gel-forming agents for the preparation of a gel are carbomer, xanthan gum, carrageenan, acacia gum, guar gum, agar-agar, alginates and tyloses, magnesium aluminium silicates, carboxymethyl cellulose, hydroxyethyl cellulose, quaternized cellulose, quaternized guar, certain polyacrylates, such as acrylates/C10-30 alkyl acrylate cross polymer, polyvinyl alcohol, polyvinylpyrrolidone.

Specially preferred are xanthan gum, carbomer, ammonium acryloyldimethyltaurate/VP copolymer ammonium acryloyldimethyltaurate/beheneth-25 methacrylate crosspolymer acrylates/C12-22 alkyl methacrylate copolymer, magnesium aluminium silicate, sodium acrylate/sodium acryloyldimethyl taurate copolymer, hydroxyethyl acrylate/sodium acryloyl dimethyl taurate copolymer, polyester-5 and acrylates/vinyl neodeconoate crosspolymer, sodium polyacrylate, polyacrylamide/C13-14 isoparaffin/laureth 7/styrene/acrylate copolymer sodium lauryl sulfate.

For the preparation of sun products it is moreover advantageous to use in a composition together with the inventive tanning ingredients corresponding water and/or oil soluble UVA or UVB filters or both. Advantageous oil-soluble UVB filters include 4-amino benzoic acid derivatives such as 4-(dimethylamino)-benzoic acid-(2-ethyl-hexyl) ester; esters of cinnamic acid such as 4-methoxy cinnamic acid (2-ethylhexyl) ester, benzophenone derivatives such as 2-hydroxy-4-methoxy benzophenone.

Preferred oil-soluble UV filters are butyl-methoxybenzoylmethane, ethylhexyl methoxycinnamate, ethylhexyl salicylate, and bis-ethyl hexyl phenol methoxyphenyl triazine.

Water-soluble UVB filters are, for example, sulfonic acid derivatives of benzophenone or of 3-benzylidene camphor or salts, such as Na or K salts, of 2-phenyl benzimidazole-5-sulfonic acid.

UVA filters include dibenzoyl methane derivatives such as butyl-methoxybenzoylmethane.

Specially preferred are butyl methoxydibenzoylmethane, ethylhexyl methoxycinnamate, ethylhexyl salicylate, octocrylene, ethylhexyl methoxycinnamate, isoamyl-p-methoxycinnamate, ethylhexyltriazone, diethylhexyl butamido triazone, methylene bis-benzotriazolyl tetramethylbutylphenol, disodium phenyl dibenzimidazole tetrasulfonate, bis-ethylhexyloxyphenol methoxyphenyl triazine, benzophenone-3. Inorganic pigments as sunscreen filters are metal oxides such as $TiO_2$, $SiO_2$, $Fe_2O_3$, $ZrO_2$, MnO, $Al_2O_3$, which can also be used in mixtures thereof.

Mixtures of the inventive cosmetic compositions together with tanning agents are possible. Such tanning agents are e.g. isatin, glycerin aldehyde, meso-tartaric acid aldehyde, glutaraldehyde, erythrulose, pirazoline-4,5-dion derivatives, dihydroxy-acetone (DHA), 4,4-dihydroxy pirazoline-5-dion derivatives.

Compositions of the invention can also comprise humectants such as glycerin, butylene glycol, propylene glycol and mixtures thereof.

Compositions of the invention can also comprise moisturising, pore tightening or firming agents, mostly from plants and algae, e.g. hazel water, *Pisum Sativum* (Pea) Extract.

Further ingredients of the cosmetic compositions of the present invention are oils, emulsifiers, esters and pigments.

Oils used for the invention can be usual cosmetic oils such as mineral oil, hydrogenated polyisobutene, squalane from synthetic or natural sources, saturated or unsaturated vegetable oils, or mixtures of two or more thereof.

Especially suitable oils are, for example, silicone oils, mineral oils, hydrogenated polyisobutene, polyisoprene, squalane, tridecyltrimellitate, trimethylpropane triisostearate, isodecylcitrate, neopentyl glycol diheptanoate, PPG-15-stearyl ether, calendula oil, jojoba oil, avocado oil, macadamia nut oil, castor oil, cocoa butter, Inca inchi oil, coconut oil, corn oil, cotton seed oil, olive oil, palm kernel oil, rapeseed oil, safflower seed oil, sesame seed oil, soybean oil, sunflower seed oil, wheat germ oil, grape kernel oil, kukui nut oil, buriti oil, calendula oil, thistle oil and mixtures thereof.

Depending upon the oils selected, the cosmetic properties of the solid composition such as softness, hardness or spreading effects are affected.

Suitable esters of polyols are esters of $C_{10}$-$C_{15}$ fatty acids and alcohols, esters of $C_{10}$-$C_{15}$ fatty acids and glycols, or esters of hydroxy fatty acids. Branched $C_{12}$-$C_{15}$ alkyl esters in conjunction with other esters such as di- or tri-esters of polyols are particularly advantageous in the oil phase, with esters of linear-chain alcohols and branched acids being particularly favourable. All these suitable esters are derived from primary alcohols. Preferred esters are dicaprylyl carbonate/decyl cocoate, diisopropyl sebacate/dibutyl adipate and isopropyl palmitate.

Suitable substances for the oil phase include Isohexadecane, PEG-40-stearate, sorbitan tristearate, behenyl alcohol, neopentyl glycol diheptanoate, propylene glycol dicaprylate, dioctyl adipate, cococaprylate/caprate, diethylhexal adipate, diisopropyl dimer dilinoleate, diisostearyl dimer dilinoleate, isohexadecane, *butyrospermum parkii* (shea) butter, $C_{12-13}$ alkyl lactate, Di-$C_{12-13}$ alkyl tartrate, Tri-$C_{12-13}$ alkyl citrate, $C_{12-15}$ alkyl lactate, PPG dioctanoate, diethylene glycol dioctanoate, meadowfoam oil, Babassu Oil, Jojoba Oil, rice Oil, $C_{12-15}$ alkyl oleate, Avocado Oil, tridecyl neopentanoate, Beeswax, betearyl alcohol and polysorbate 60, $C_{18-26}$ triglycerides, cetearyl alcohol & cetearyl glucoside, acetylated lanolin, VP/eicosene copolymer, glyceryl hydroxystearate, $C_{18-36}$ acid glycol ester, with substances such as $C_{18-36}$ triglycerides, caprylic/capric triglyceride, glyceryl hydroxystearate and mixtures thereof. Also suitable and preferred are cetyl alcohol & glyceryl stearate & PEG 75 stearate & ceteth-20 & steareth-20, lauryl glucoside & polyglyceryl-2 dipolyhydroxystearate, beheneth-25, polyamide-3 & pentaerythrityl tetra-Di-T-butyl hydroxycinnamate, polyamide-4, PEG-100 stearate, potassium cetylphosphate, stearic acid and hectorites.

Cosmetic compositions according to the invention may preferably exist as O/W or W/O emulsions as well as emulsion from the above-mentioned type of multiple, micro or nano emulsions. Suitable emulsifiers for O/W emulsions are for instance addition products of 2-30 mol ethylene oxide to linear $C_8$-$C_{22}$ fatty alcohols, to $C_{12}$-$C_{22}$ fatty acids and to $C_8$-$C_{15}$ alkylphenols; $C_{12}$-$C_{22}$ fatty acid monoesters and diesters of addition products of 1-30 mol ethylene oxide to glycerin; glycerin monoesters and diesters as well as sorbitan monoester and diester of $C_6$-$C_{22}$ fatty acids, polyol- and polyglycerin ester; addition products of ethylene oxide to castor oil; as well as ampholytic tensides.

Suitable emulsifiers for W/O emulsions are for instance addition products of 2-15 mol ethylene oxide to castor oil, esters of $C_{12}$-$C_{22}$ fatty acids and glycerin, polyglycerin, glycols, pentaerythrite, sugar alcohols (e.g. sorbite), polyglucosides (e.g. cellulose), polyalkylene glycols, wool alcohols, copolymers of polysiloxan polyalkyl polyether.

Suitable emulsifiers for multiple emulsions and micro emulsions are for instance tribehenin PEG-20 esters, PEG-12 dimethicone crosspolymer, lauryl PEG/PPG-18/18 methicone, PEG-PPG-19/19 dimethicone including cyclopentasiloxane, polyglyceryl-6 dioleate and PEG-8 caprylic/capric glycerides.

Pigments, pigment mixtures or powders with a pigment-like effect, also including those with a pearl-gloss effect, may include, for example, iron oxides, aluminium silicates such as ochre, titanium dioxide, mica, kaolin, manganese containing clays, silicium dioxide, zinc oxide, calcium carbonate, French chalk, mica-titanium oxide, mica-titanium oxide-iron oxide, nylon beads, ceramic beads, expanded and non-expanded synthetic polymer powders, powdery natural organic compounds such as milled solid algae, milled plant parts, encapsulated and non-encapsulated cereal starches and mica-titanium oxide-organic dye.

Further cosmetic auxiliaries are waxes.

The waxes may be selected among natural plant waxes, animal waxes, natural and synthetic mineral waxes and synthetic waxes. Included are carnauba wax, candelilla wax, ozokerite, beeswax, montan wax, wool wax, ceresine, micro waxes, paraffin waxes, petrolatum, silicon wax, polyethylene glycol waxes or polyethylene glycol-ester waxes.

A further object of the invention is the cosmetic use of a cosmetic composition for increasing the collagen synthesis in skin, wherein the composition comprises 0.001-0.5 wt % of a *Phaeodactylum tricornutum* extract; 0.00001-2.0 wt %, preferably 0.00005-2.0 wt % of dimer tripeptide-43 or hydrolyzed rice protein, the percentages being related to the total weight of the composition; and cosmetic auxiliaries or mixtures thereof up to a total of 100 wt % of the composition.

Specially preferred is the use of a cosmetic composition, wherein the composition comprises
 (1) 0.001-0.5 wt % of a *Phaeodactylum tricornutum* extract;
 (2) 0.00001-2.0 wt %, preferably 0.00005-2.0 wt % of dimer tripeptide-43 or hydrolyzed rice protein;
 (3) 0.1-9.0 wt % of one or more substances which have an enhancing effect to the collagen I synthesis; all concentrations being related to the total weight of the composition; and
 (4) further cosmetic auxiliaries or mixtures thereof up to a total of 100 wt % of the composition.

A further object of the invention is a method for increasing the collagen I synthesis in skin cells by applying to the skin a composition comprising 0.001-0.5 wt % of a *Phaeodactylum tricornutum* extract; 0.00001-2.0 wt %, preferably 0.00005-2.0 wt % of dimer tripeptide-43 or hydrolyzed rice protein, the concentrations being related to the total weight of the composition; and cosmetic auxiliaries or mixtures thereof up to a total of 100 wt % of the composition.

Specially preferred is a method, wherein the composition comprises
 (1) 0.001-0.5 wt % of a *Phaeodactylum tricornutum* extract;
 (2) 0.00001-2.0 wt %, preferably 0.00005-2.0 wt % of dimer tripeptide-43 or hydrolyzed rice protein;
 (3) 0.1-9.0 wt % of one or more substances which have an enhancing effect on collagen I synthesis; all concentrations being related to the total weight of the composition; and
 (4) further cosmetic auxiliaries and mixtures thereof up to a total of 100 wt % of the composition.

The invention shall now be described in detail for the cosmetic composition of the invention by examples. All figures given as percentages are % by weight if not specified otherwise.

EXAMPLES 1 TO 3

Day Creme

| Phase A | | | |
|---|---|---|---|
| | Example 1 | Example 2 | Example 3 |
| Tribehenin PEG-20 Esters | 2.9 | 3.2 | 3.1 |
| Cetearyl Alcohol & Cetearyl Glucoside | 3.4 | 3.3 | 3.1 |
| Caprylic/Capric Triglyceride | 5 | 4 | 6 |
| Isohexadecane | 3 | 4 | 2 |
| *Butyrospermum Parkii* (Shea Butter) | 3.5 | 3.0 | 4.5 |
| Beeswax | 1.5 | 1.8 | 1.6 |

| Phase B | | | |
|---|---|---|---|
| | Example 1 | Example 2 | Example 3 |
| Water | q.s. ad 100 | q.s. ad 100 | q.s. ad 100 |
| Glycerin | 5.5 | 8 | 3.5 |
| Xanthan Gum | 0.2 | 0.4 | 0.5 |
| Mica & TiO$_2$ | 0.1 | 0.2 | 0.3 |
| Bis-PEG-18 Methyl Ether Dimethyl Silane | 4 | 4.9 | 3 |

| Phase C | | | |
|---|---|---|---|
| | Example 1 | Example 2 | Example 3 |
| Radical scavenging complex* | 0.2 | 0.5 | — |
| Hydrolysed Soy Flour | 0.02 | 0.03 | — |
| Sodium Hyaluronate | 0.005 | 0.002 | — |
| Acetyl Dipeptide-1 Cetyl Ester | 0.006 | 0.01 | — |
| Hexapeptide-11 | 0.09 | 0.08 | — |
| Acrylates/C12-22 Alkyl Methacrylate Copolymer & Water & Pentylene Glycol | 0.05 | 0.2 | — |
| *Kigelia Africana* Fruit Extract | 0.01 | 0.05 | — |
| Caprylic/Capric Triglyceride & *Phaeodactylum Tricornutum* Extract & Tocopherol (Megassane) | 0.03 | 0.07 | 0.5 |
| Aqua & Dimer Tripeptide-43 & Butylene Glycol (Prolixir S20 ®) | 0.4 | 0.7 | 0.8 |
| Polyacrylamide & C13-14 Isoparaffin & Laureth 7 | 1.0 | 1.3 | 1.6 |
| Triethanolamine (pH adjuster) | q.s. | q.s. | q.s. |
| Preservative | q.s. | q.s. | q.s. |
| Perfume/Fragrance | 0.2 | 0.1 | |

*Coffee Arabica Seed Extract (2%), Green Tea Leaf Extract (2%), Angelica Archan-gelica Root Extract (2%), Pongamia Pinnata Seed Extract (2%), Lecithine, Ethanol (6%), Tocopherol, Ascorbyl Palmitate, Citric Acid, Ascorbic Acid, Water, PEG-8.

The ingredients of phase A are mixed and heated up to 70-75° C. while stirring. The ingredients of phase B are separately mixed and heated up to 70-75° C. while stirring. Phase A is added to Phase B, emulsifying while stirring at the same temperature. Then the emulsion is cooled down and the separately prepared Phase C is added to the mixture while stirring to homogeneity at temperatures of about 30-35° C.

EXAMPLES 4 TO 6

Day Creme

| Phase A | | | |
|---|---|---|---|
| | Example 4 | Example 5 | Example 6 |
| Tribehenin PEG-20 Esters | 2.9 | 3.2 | 3.1 |
| Cetearyl Alcohol & Cetearyl Glucoside | 3.4 | 3.3 | 3.1 |
| Caprylic/Capric Triglyceride | 5 | 4 | 6 |
| Isohexadecane | 3 | 4 | 2 |
| *Butyrospermum Parkii* (Shea Butter) | 3.5 | 3.0 | 4.5 |
| Beeswax | 1.5 | 1.8 | 1.6 |

-continued

| Phase B | | | |
|---|---|---|---|
| | Example 4 | Example 5 | Example 6 |
| Water | q.s. ad 100 | q.s. ad 100 | q.s. ad 100 |
| Glycerin | 5.5 | 8 | 3.5 |
| Xanthan Gum | 0.2 | 0.4 | 0.5 |
| Mica & TiO$_2$ | 0.1 | 0.2 | 0.3 |
| Bis-PEG-18 Methyl Ether Dimethyl Silane | 4 | 4.9 | 3 |

| Phase C | | | |
|---|---|---|---|
| | Example 4 | Example 5 | Example 6 |
| Radical scavenging complex* | 0.2 | 0.5 | — |
| Hydrolysed Soy Flour | 0.02 | 0.03 | — |
| Sodium Hyaluronate | 0.005 | 0.002 | — |
| Acetyl Dipeptide-1 Cetyl Ester | 0.006 | 0.01 | — |
| Hexapeptide-11 | 0.09 | 0.08 | — |
| Acrylates/C12-22 Alkyl Methacrylate Copolymer & Water & Pentylene Glycol | 0.05 | 0.2 | — |
| Kigelia Africana Fruit Extract | 0.01 | 0.05 | — |
| Caprylic/Capric Triglyceride & Phaeodactylum Tricornutum Extract & Tocopherol (Megassane) | 0.03 | 0.07 | 0.5 |
| Water & Glycerin & Hydrolyzed Rice Protein (Prolixir ICE) | 0.4 | 0.7 | 0.8 |
| Polyacrylamide & C13-14 Isoparaffin & Laureth 7 | 1.0 | 1.3 | 1.6 |
| Triethanolamine (pH adjuster) | q.s. | q.s. | q.s. |
| Preservative | q.s. | q.s. | q.s. |
| Perfume/Fragrance | 0.2 | 0.1 | — |

*Coffee Arabica Seed Extract (2%), Green Tea Leaf Extract (2%), Angelica Archangelica Root Extract (2%), Pongamia Pinnata Seed Extract (2%), Lecithine, Ethanol (6%), Tocopherol, Ascorbyl Palmitate, Citric Acid, Ascorbic Acid, Water, PEG-8.

The ingredients of phase A are mixed and heated up to 70-75° C. while stirring. The ingredients of phase B are separately mixed and heated up to 70-75° C. while stirring. Phase A is added to Phase B, emulsifying while stirring at the same temperature. Then the emulsion is cooled down and the separately prepared Phase C is added to the mixture while stirring to homogeneity at temperatures of about 30-35° C.

EXAMPLE 7

Comparative Test

Collagen-I by Western Blot

Normal fibroblasts were treated for 6 days with the ingredients A, B and C alone or in combination, respectively, diluted in culture medium. Then collagen was extracted and collagen I was detected by using immunoblotting method with a chemiluminescence detection kit. The intensity of the bands of collagen I obtained on the treated cells was compared to the intensity of the bands of the non-treated cells. Moreover, the intensity of the bands was quantified by using an image analysis software.

Figure 1A:
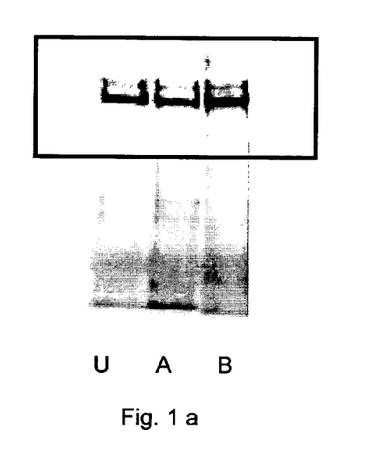
FIG. 1a Chromatographic results for ingredients A and B separately after Western Blot test of normal human fibroblasts for collagen I FIG. 1b Column diagram of the results according to FIG. 1a after image analysis FIG. 2a Chromatographic results for ingredients A and B together after Western Blot test of normal human fibroblasts for collagen I FIG. 2b Column diagram of the results according to FIG. 2a after image analysis FIG. 3 Column diagram of the results according to FIGS. 1b and 2b and a group of collagen boosters FIG. 4 Results of ultrasonic measurements of Dermis density of 16 females following 4 weeks of twice daily application of the cream of Example 1 of the invention
Figure 1B:
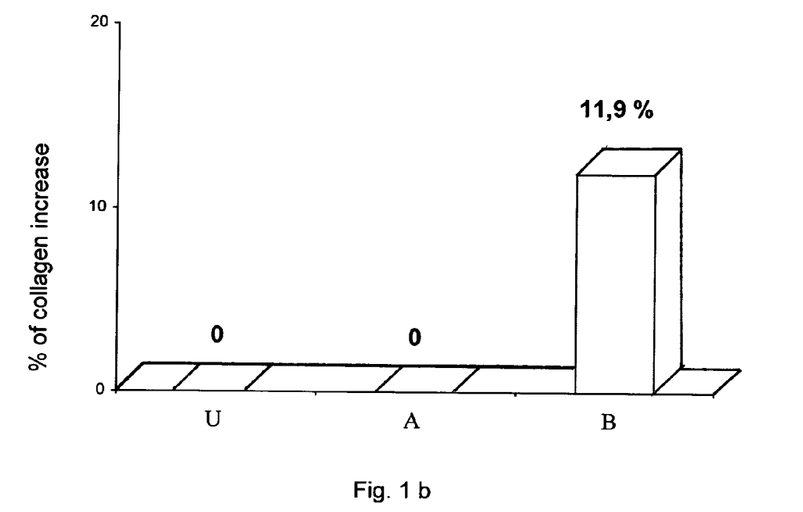
Figure 2:
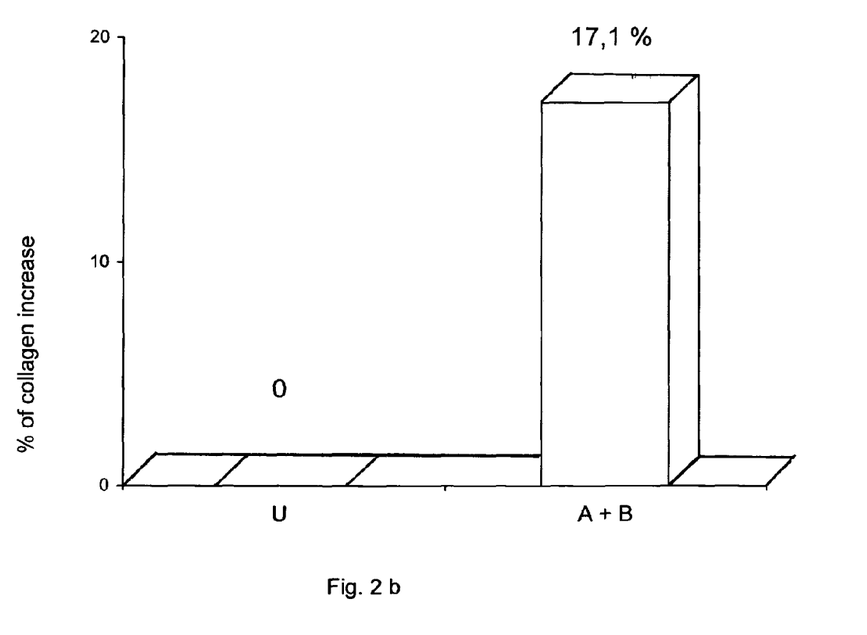
Figure 2A:
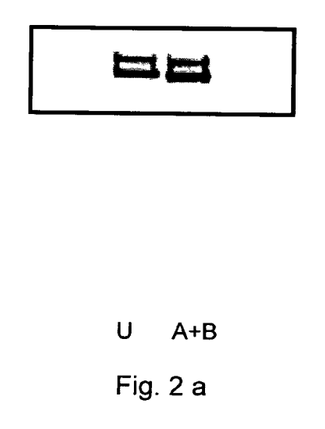
Figure 3:
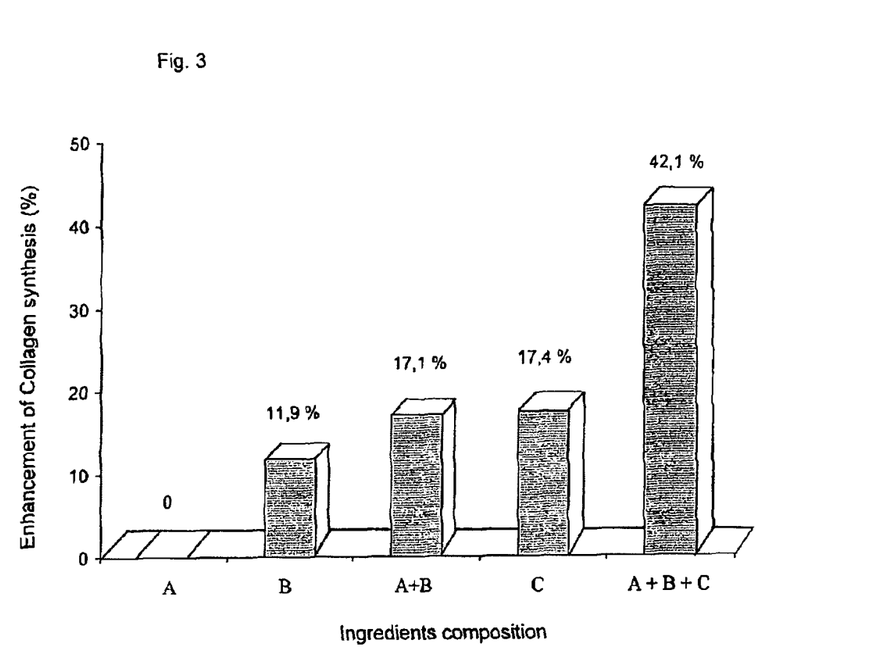

The results are presented in FIG. 1 to FIG. 3.

The in vitro Western Blotting collagen-I synthesis shows the following results after an image analysis (1) Ingredient A=Dimer Tripeptide-43 0.005% by weight: no activity
  The concentration corresponds to 0.5% by weight of e.g. Prolixir S 20®.
(2) Ingredient B=*Phaeodactylum tricornutum* extract 0.00025%=2.5 μg/ml: 11.9%
  The concentration corresponds to 0.005% by weight of e.g. Meggassane®.

The results of (1) and (2) are also demonstrated in FIG. 1a and FIG. 1b. "U"=untreated (control), A and B are the ingredients.

(3) Ingredients A and B=
  0.005% by weight of Dimer Tripeptide-43+0.00025% by weight of *Phaeodactylum tricornutum* extract (2.5 μg/ml): 17.1%
  The results show a first synergistic effect by enhancement from 11.9% to 17.1% after addition of ingredient A without activity. The results are demonstrated in FIG. 2a and FIG. 2b. "U"=untreated (control), A and B are the ingredients.
(4) Ingredients C=collagen boosters
  The collagen boosters are a mixture of 6 ppm N-Acetyl-Try-Arg-O-Hexadecyl Ester+0.015% by weight of Hydrolysed Soy Flour+0.05% by weight of Hexapeptide-11+0.005% by weight of *Kigelia Africana* Fruit Extract: 17.4%
(5) Ingredients A, B and C with the same concentrations as in (1), (2) and (4): 42.1%
  The results show a second synergistic effect between the main actives (ingredients) A and B and a group of collagen boosters by enhancement from 17.1% (ingredients A+B) after addition of ingredients C with 17.4% effect to a total effect of 42.1%. All results together are demonstrated in FIG. 3. "U"=untreated (control): A, B and C, respectively, are the ingredients.

EXAMPLE 8

Clinical Study on Caucasian Women

It was the aim of the clinical study to assess the structural changes occurring in the dermis after 4 weeks of daily application of the composition of the invention onto face and neck.

The test panel included 16 females aged from 40 up to 59. The mean age of the whole test panel was 49±2 (mean+sem). All the volunteers belong to Caucasian phototype.

The test was based on ultrasonographic measurements. The Dermascan-C system (Cortex Technology, Hadsund, Denmark) was used to obtain a sequence of closely spaced B-scan images of temple. At the measuring time, 3 measurements on the same defined area were performed. For each acquisition, the software calculated the different parameters: total area of the dermis (A), LEP, MEP and HEP and results were expressed as LEP/A, MEP/A and HEP/A.

LEP=the area of intensities 0 to 30 pixels which correspond to low echogenic pixels;

MEP=the area of intensities 31 to 80 pixels which correspond to moderate echogenic pixels;

HEP=the area of intensities 81 to 255 pixels which correspond to high echogenic pixels.

Figure 4:
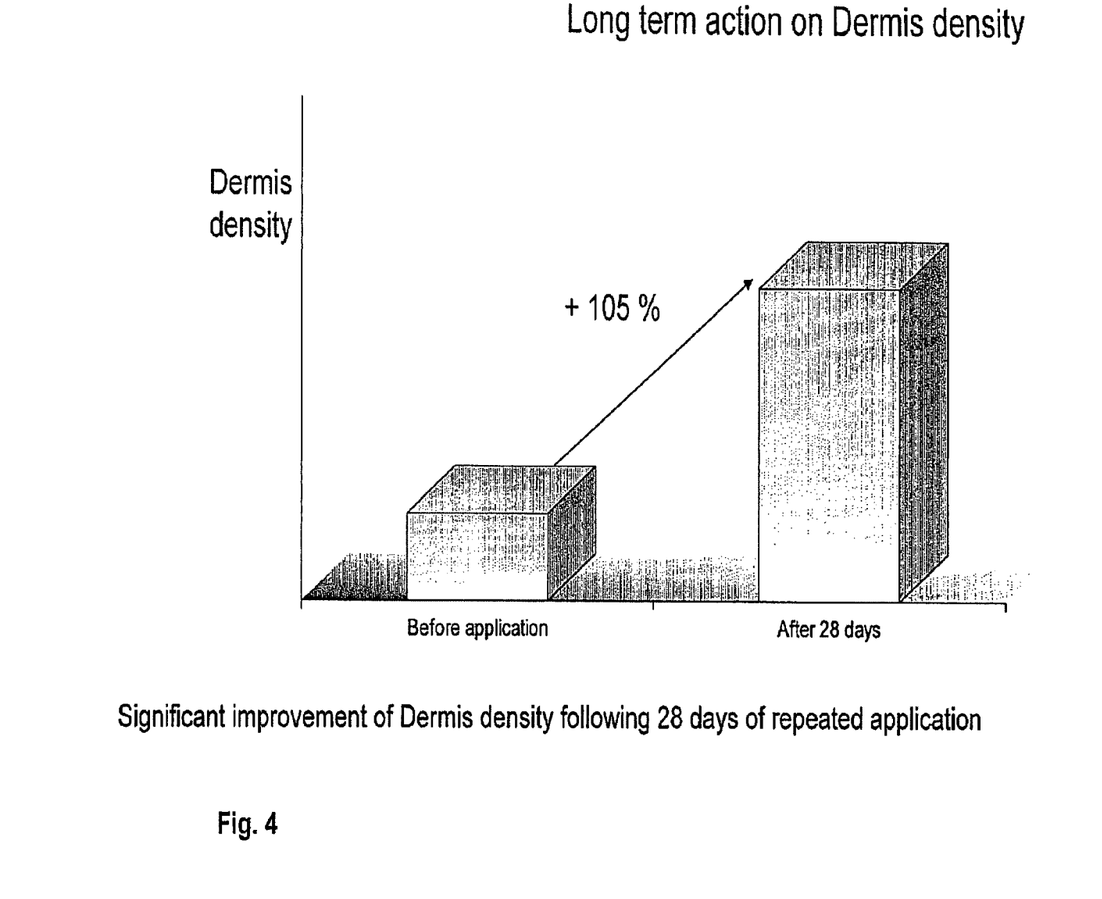

The results are given in FIG. 4.

The invention claimed is:

1. A cosmetic composition for use in increasing the collagen synthesis in skin comprising:
  0.001-0.5 wt % of a *Phaeodactylum tricornutum* extract;
  0.00001-2.0 wt % of dimer tripeptide-43, the concentrations being related to the total weight of the composition; and
  cosmetic auxiliaries or mixtures thereof up to a total of 100 wt % of the composition.

2. The cosmetic composition according to claim 1 comprising 0.01 to 1.0 wt % of a radical scavenger.

3. The cosmetic composition according to claim 1 comprising 0.00005-2.0 wt % of dimer tripeptide-43.

4. A method for increasing collagen I synthesis in skin cells, the method comprising applying a composition to the skin cells, wherein the composition comprises:
0.001-0.5 wt % of a *Phaeodactylum tricornutum* extract;
0.00001-2.0 wt % of Dimer Tripeptide-43 or Hydrolyzed Rice Protein, the concentrations being related to the total weight of the composition; and
cosmetic auxiliaries or mixtures thereof up to a total of 100 wt % of the composition.

5. The method according to claim 4, wherein the composition comprises:
(1) 0.001-0.5 wt % of a *Phaeodactylum Tricornutum* Extract;
(2) 0.00001-2.0 wt % of Dimer Tripeptide-43 or Hydrolyzed Rice Protein;
(3) 0.1-9.0 wt % of one or more substances which have an enhancing effect to collagen I synthesis; all concentrations being related to the total weight of the composition; and
(4) further cosmetic auxiliaries or mixtures thereof up to a total of 100 wt % of the composition.

6. The cosmetic composition according to claim 2, wherein the radical scavenger is a liposomal preparation of four plant extracts comprising:
1-4% *Camelia sinensis* leaf extract,
1-4% *Coffea arabica* seed extract,
1-4% *Pongamia pinnata* seed extract, and
1-4% *Angelica archangelica* root extract.

7. A cosmetic composition for use in increasing the collagen synthesis in skin comprising
(1) 0.001-0.5 wt % of a *Phaeodactylum tricornutum* extract;
(2) 0.00001-2.0 wt % of dimer tripeptide-43;
(3) 0.1-9.0 wt % of one or more substances which have an enhancing effect to collagen I synthesis; all concentrations being related to the total weight of the composition; and
(4) further cosmetic auxiliaries or mixtures thereof up to a total of 100 wt % of the composition.

8. The cosmetic composition according to claim 7, wherein the substances with enhancing effect are at least one selected from the group consisting of dipeptides, hexapeptides, plant extracts, Soybean flour, and mixtures thereof.

9. The cosmetic composition according to claim 7, wherein the substances with enhancing effect are selected from the group consisting of acetyl dipeptide-1 cetyl ester, hexapeptide-11, hydrolysed soybean flour, *Kigelia africana* fruit extract and mixtures thereof.

10. The cosmetic composition according to claim 7 comprising 0.01 to 1.0 wt % of a radical scavenger.

11. The cosmetic composition according to any one of claim 10, wherein the radical scavenger is a liposomal preparation of four plant extracts comprising:

| | |
|---|---|
| 1-4% | *Camelia sinensis* leaf extract, |
| 1-4% | *Coffea arabica* seed extract, |
| 1-4% | *Pongamia pinnata* seed extract, and |
| 1-4% | *Angelica archangelica* root extract. |

12. The cosmetic composition according to claim 7 comprising 0.00005-2.0 wt % of dimer tripeptide-43.

* * * * *